United States Patent
Shah et al.

(10) Patent No.: US 10,143,654 B2
(45) Date of Patent: *Dec. 4, 2018

(54) CONTROLLED-RELEASE COMPOSITIONS OF MELATONIN COMBINED WITH SEDATIVE AND/OR ANALGESIC INGREDIENTS

(71) Applicant: Physician's Seal, LLC, Boca Raton, FL (US)

(72) Inventors: Syed M. Shah, Boca Raton, FL (US); Daniel Hassan, Boca Raton, FL (US); Christopher Diorio, Boca Raton, FL (US); Fred Hassan, Boca Raton, FL (US)

(73) Assignee: Physician's Seal, LLC, Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/371,868

(22) Filed: Dec. 7, 2016

(65) Prior Publication Data

US 2017/0079919 A1   Mar. 23, 2017

Related U.S. Application Data

(60) Division of application No. 15/148,665, filed on May 6, 2016, now Pat. No. 9,532,952, which is a continuation-in-part of application No. 14/942,299, filed on Nov. 16, 2015, now Pat. No. 9,549,900, which is a division of application No. 14/186,599, filed on Feb. 21, 2014, now Pat. No. 9,186,351, which is a continuation of application No. 13/359,638, filed on Jan. 27, 2012, now Pat. No. 8,691,275.

(60) Provisional application No. 61/437,217, filed on Jan. 28, 2011.

(51) Int. Cl.
```
A61K 9/16       (2006.01)
A61K 31/7034    (2006.01)
A61K 31/4045    (2006.01)
A61K 36/76      (2006.01)
A61K 36/84      (2006.01)
A61K 9/20       (2006.01)
A61K 45/06      (2006.01)
```

(52) U.S. Cl.
CPC .......... *A61K 9/1652* (2013.01); *A61K 9/2013* (2013.01); *A61K 9/2031* (2013.01); *A61K 9/2054* (2013.01); *A61K 9/2059* (2013.01); *A61K 9/2077* (2013.01); *A61K 31/4045* (2013.01); *A61K 31/7034* (2013.01); *A61K 36/76* (2013.01); *A61K 36/84* (2013.01); *A61K 45/06* (2013.01)

(58) Field of Classification Search
None
See application file for complete search history.

(56) References Cited

U.S. PATENT DOCUMENTS

| | | |
|---|---|---|
| 4,600,723 A | 7/1986 | Short et al. |
| 4,665,086 A | 5/1987 | Short et al. |
| 4,687,667 A | 8/1987 | Rhodes et al. |
| 4,687,763 A | 8/1987 | Wurtman |
| 4,786,505 A | 11/1988 | Lovgren et al. |
| 4,855,313 A | 8/1989 | Welch et al. |
| 5,362,745 A | 11/1994 | Graziella |
| 5,418,010 A | 5/1995 | Janda et al. |
| 5,449,683 A | 9/1995 | Wurtman |
| 5,498,423 A | 3/1996 | Zisapel |
| 5,552,418 A | 9/1996 | Depreux et al. |
| 5,641,801 A | 6/1997 | Wurtman |
| 5,688,520 A | 11/1997 | Karsenty et al. |
| 5,707,652 A | 1/1998 | Lewy et al. |
| 5,846,939 A | 12/1998 | Miclo et al. |
| 5,856,529 A | 1/1999 | Catt et al. |
| 5,879,710 A | 3/1999 | Bromet |
| 6,034,239 A | 3/2000 | Ohkawa et al. |
| 6,075,045 A | 6/2000 | Nishino et al. |
| 6,214,377 B1 | 4/2001 | Dittgen et al. |
| 6,306,435 B1 | 10/2001 | Chen et al. |
| 6,365,185 B1 | 4/2002 | Ritschel et al. |
| 6,383,526 B1 | 5/2002 | Andrews et al. |
| 6,423,349 B1 | 7/2002 | Sherratt et al. |
| 6,469,044 B1 | 10/2002 | Zisapel |

(Continued)

FOREIGN PATENT DOCUMENTS

| | | |
|---|---|---|
| CN | 102731587 A | 4/2015 |
| EP | 0015334 B1 | 5/1982 |

(Continued)

OTHER PUBLICATIONS

Wikipedia entry for GABA receptor agonist, downloaded May 15, 2017 from https://en.wikipedia.org/wiki/GABA_receptor_agonist.*
Hsiupei Chen, et al. Contemporary Management of Neuropathic Pain for the Primary Care Physician. Mayo Clin Proc. 2004;79(12):1533-1545.*
Wikipedia entry for Valerian (herb), downloaded May 15, 2017, from https://en.wikipedia.org/wiki/Valerian_(herb).*
Needham, Thomas E. "The Solubility of Amino Acids in Various Solvent Systems", Ph.D. Dissertation, University of Rhode Island, 1970, p. 49. (Year: 1970).*

(Continued)

*Primary Examiner* — Michael P Cohen
(74) *Attorney, Agent, or Firm* — Christopher M. Ramsey; GrayRobinson, P.A.

(57) ABSTRACT

Controlled-release therapeutic compositions including melatonin combined with sedative and/or analgesic ingredients are described. The compositions have a solid core including melatonin in an acidified polymeric matrix. A sedative ingredient such as GABA receptor agonist may also be in the acidified polymeric matrix. The composition may include an expedited release portion providing a burst release of active ingredients and a sustained release portion providing a sustained release of active ingredients.

16 Claims, 3 Drawing Sheets

Specification includes a Sequence Listing.

(56) References Cited

U.S. PATENT DOCUMENTS

| | | |
|---|---|---|
| 6,566,389 B1 | 5/2003 | Zisapel et al. |
| 6,638,963 B1 | 10/2003 | Lewy et al. |
| 6,703,412 B1 | 3/2004 | Rosenthal |
| 6,726,927 B2 | 4/2004 | Chen |
| 6,794,407 B2 | 9/2004 | Lewy et al. |
| 6,833,383 B2 | 12/2004 | Zisapel |
| 7,115,282 B2 | 10/2006 | Shefer et al. |
| 7,332,177 B1 | 2/2008 | Zisapel et al. |
| 7,455,864 B2 | 11/2008 | Heuer et al. |
| 7,476,405 B2 | 1/2009 | Gardiner et al. |
| 7,670,619 B2 | 3/2010 | Mihaylov |
| 7,670,624 B2 | 3/2010 | Tsutsumi et al. |
| 7,713,551 B2 | 5/2010 | McGurk et al. |
| 7,790,755 B2 | 9/2010 | Akiyama et al. |
| 7,799,817 B2 | 9/2010 | Cremisi |
| 7,803,817 B2 | 9/2010 | Kostadinov et al. |
| 7,838,027 B2 | 11/2010 | Rao et al. |
| 7,858,656 B2 | 12/2010 | Stankov |
| 7,906,154 B2 | 3/2011 | Heuer et al. |
| 7,914,826 B2 | 3/2011 | Heuer et al. |
| 8,075,914 B2 | 12/2011 | Zisapel et al. |
| 8,512,769 B2 | 8/2013 | Sievers et al. |
| 8,642,648 B2 | 2/2014 | Tanoue et al. |
| 8,691,275 B2 | 4/2014 | Shah et al. |
| 8,728,511 B2 | 5/2014 | Zisapel et al. |
| 8,785,492 B2 | 7/2014 | Dressman et al. |
| 8,809,395 B2 | 8/2014 | Mulzer et al. |
| 8,821,926 B2 | 9/2014 | Marunaka et al. |
| 9,060,995 B2 | 6/2015 | Dressman et al. |
| 9,532,952 B2 * | 1/2017 | Shah .............. A61K 9/1652 |
| 2001/0038863 A1 | 11/2001 | Jaenicke et al. |
| 2002/0015731 A1 | 2/2002 | Appel et al. |
| 2002/0114832 A1 | 8/2002 | Herrmann et al. |
| 2002/0119191 A1 | 8/2002 | Nishino et al. |
| 2002/0132006 A1 | 9/2002 | Sue et al. |
| 2003/0040539 A1 | 2/2003 | Zisapel |
| 2003/0143272 A1 | 7/2003 | Waterman |
| 2003/0207851 A1 | 11/2003 | Wei |
| 2004/0062778 A1 | 4/2004 | Shefer et al. |
| 2004/0248966 A1 | 12/2004 | Zisapel |
| 2005/0019400 A1 * | 1/2005 | Deveney .............. A61K 9/2072 424/468 |
| 2005/0069579 A1 | 3/2005 | Kamaguchi et al. |
| 2005/0129783 A1 | 6/2005 | McCleary et al. |
| 2005/0164957 A1 | 7/2005 | Barberich |
| 2005/0281876 A1 | 12/2005 | Li et al. |
| 2006/0009465 A1 | 1/2006 | Edgar et al. |
| 2006/0210631 A1 | 9/2006 | Patel et al. |
| 2006/0217489 A1 | 9/2006 | Yako et al. |
| 2006/0257469 A1 | 11/2006 | Bulka |
| 2007/0087053 A1 | 4/2007 | Hayward |
| 2007/0098777 A1 | 5/2007 | Nishino et al. |
| 2007/0196348 A1 | 8/2007 | Gardiner et al. |
| 2007/0231388 A1 | 10/2007 | Anstett-Klein et al. |
| 2007/0292510 A1 | 12/2007 | Huang |
| 2008/0020039 A1 * | 1/2008 | Parikh .............. A61K 9/209 424/472 |
| 2008/0134807 A1 | 6/2008 | May |
| 2008/0139510 A1 | 6/2008 | Rose |
| 2008/0166416 A1 | 7/2008 | Lizio et al. |
| 2008/0171085 A1 | 7/2008 | Elnekave et al. |
| 2008/0248141 A1 * | 10/2008 | Heuer .............. A61K 36/38 424/745 |
| 2008/0254121 A1 * | 10/2008 | Clement .............. A61K 9/167 424/472 |
| 2008/0299199 A1 | 12/2008 | Bar-Shalom et al. |
| 2009/0004262 A1 | 1/2009 | Shaw et al. |
| 2009/0004281 A1 | 1/2009 | Nghiem et al. |
| 2009/0047347 A1 | 2/2009 | Maggio |
| 2009/0227670 A1 | 9/2009 | Berg |
| 2009/0238905 A1 | 9/2009 | Gurney et al. |
| 2009/0246301 A1 | 10/2009 | Ehrenpreis et al. |
| 2010/0092562 A1 * | 4/2010 | Hollenbeck ......... A61K 9/0095 424/488 |
| 2010/0119601 A1 | 5/2010 | McCarty |
| 2010/0197758 A1 | 8/2010 | Andrews et al. |
| 2010/0298379 A1 | 11/2010 | Jacobsen |
| 2011/0053866 A1 | 3/2011 | Duffield et al. |
| 2011/0064712 A1 | 3/2011 | Amato |
| 2011/0064830 A1 | 3/2011 | Piotrowski |
| 2011/0081451 A1 | 4/2011 | Siegel et al. |
| 2012/0207842 A1 | 8/2012 | Shah et al. |
| 2012/0277323 A1 | 11/2012 | Kumar et al. |
| 2012/0301541 A1 | 11/2012 | Haronsky et al. |
| 2012/0301546 A1 | 11/2012 | Hassan |
| 2013/0028943 A1 | 1/2013 | McCarty |
| 2013/0116215 A1 | 5/2013 | Coma et al. |
| 2014/0127287 A1 | 5/2014 | Xiong et al. |
| 2014/0271890 A1 | 9/2014 | Ahmad |
| 2014/0314860 A1 | 10/2014 | Shah et al. |
| 2015/0250203 A1 | 9/2015 | Edwards et al. |
| 2016/0067186 A1 | 3/2016 | Shah et al. |

FOREIGN PATENT DOCUMENTS

| | | | |
|---|---|---|---|
| EP | 1743633 B1 | 8/2010 | |
| WO | 9503043 | 2/1995 | |
| WO | 9947175 A1 | 9/1999 | |
| WO | 2005027878 A1 | 3/2005 | |
| WO | 2007012856 A1 | 2/2007 | |
| WO | 2008057802 A2 | 5/2008 | |
| WO | 2008134807 A1 | 11/2008 | |
| WO | 2009077749 A1 | 6/2009 | |
| WO | 2010144943 A1 | 12/2010 | |
| WO | 2012109216 A1 | 8/2012 | |
| WO | WO 2012103411 A2 * | 8/2012 | ........... A61K 9/2013 |
| WO | 2012170488 A1 | 12/2012 | |
| WO | 2012170611 A1 | 12/2012 | |
| WO | 2014083438 A2 | 6/2014 | |

OTHER PUBLICATIONS

CAS Registry Record for Gamma-aminobutyric acid (Year: 2018).*
C Roshy Joseph, Ilanchezhian R, Patgiri Biswajyoti, CR Harish. Pharmacognostical Study of Nagakeshara (Mesua Ferrea Linn)—An Ingredient in Vyaghrihareet Aki Av Aleha. IJRAP 2010, 1 (2) 264-272. (Year: 2010).*
Addendum to NDA 21-782 Clinical Pharmacology Biopharmaceutics Review; Takeda Global Research & Development Center, Inc.; Sep. 21, 2004.
Alex Becker, Falko Felgentreff, Helmut Schroder, Beat Meier, Acel Brattstrom; "The Anxiolytic Effects of a Valerian Extract is Based on Valerenic Acid;" Becker at al BMC Complementary and Alternative Medicine; 2014.
Australian Public Assessment Report for Melatonin (pp. 1-5, Dec. 2009). Downloaded from the Internet May 17, 2014, from the site: http://www.tga.gove.au/pdf/auspar/auspar-circadin.pdf.
Baranuskiene et al., Flavor Retention of Peppermint (Mentha piperita l.) Essential Oil Spray-Dried in Modified Starches during Encapsulation and Storage, J. Agric Food Chem., 2007, 55, 3027-3036.
Benes et al., Transmucosal, Oral Controlled-Release and Transdemal Drug Administration in Human Subjects; A Crossover Study wth Melatonin, Journal of Pharmaceutical Sciences/ 1115, vol. 86, No. 10, Oct. 1997.
Birgit M. Dietz, Gail B. Mahady, Guido F. Pauli, Norman R. Farnsworth; "Valerian Extract and Valerenic Acid are Partial Agonists of the 5-HT 5a Receptor in Vitro:" Molecular Brain Research, vol. 138, pp. 191-197; May 25, 2005.
Bogentoft et al., Influence of Food on the Absorption of Acetylsaliclic Acid From Enteric-Coated Dosage Forms, European J. Clin. Pharmacol., 14, 351-355, 1978.
Cellulose acetate phthalate enter coating (enerexusa.com/articles/ enteric_coating.htm., last visit Feb. 6, 2014.
Chen et al., The Basic Strength of Carbazole, An Estimate of the Nitrogen Basicity of Pyrrole and Indole, Journal of American Chemical Society 93.20, Oct. 6, 1971, 5102-5107.
Clark et al., Variations in Composition of Peppermint Oil in Relation to Produciton Areas, Ecomonic Botany 25(1), 1981, pp. 59-69, Bronx, NY, USA.

(56) References Cited

OTHER PUBLICATIONS

Committee for Proprietary Medicinal Products, Note for Guidance on Quality of Modified Release Products; A Oral Dosage Forms, B: Transdermal Dosage Forms, Jul. 29, 199, The European Agency for the Evalu of Medicianl Products, London.
Dey et al., Multiparticulate Drug Deliver Systems for Controlled Release, Tropical Journal of Pharmaceutical Research, Sep. 2008: 7(3); 1067-1075, Pharmacotherapy Group, Faculty of Pharmacy,University of Benin, Benin City, 300001 Nigeria.
Digenis, George A., The in vivo behavior of multiparticulate versus single unit dose formulations,presented at Capsugel's Symposioum in Seoul (Apr. 10, 199) and Tokyo (Apr. 12, 1990).
Dong et al., Effect of processing parameters on the formation of spherical multinuclear microcapsules encapsulating peppermint oil by peppermint oil by coacervation, Journal of Microencapsulation, Nov. 2007: 24(7): 634-646.
Faroongsarng et al., The Swelling and Water Uptake of Tables III; Moisture Sorption Behaviour of Tablet Disintegrants, Drug Development and Industrial Pharmacy, 20(5), 779-798, (1994).
Final Report on the Safety Assessment of *Mentha piperita* (Peppermint) Oil, *Mentha piperita* (Peppermint) Leaf Extract *Mentha piperita* (Peppermint) Leaf, and *Mentha piperita* (Peppermint) Leaf Water, International Journal of Toxicology, 2001, 20:61, online version at http//ijt.sagepub.com/content20/3/_suppl/61.
Galeotti et al, Menthol; a natural analgesic compound, Neuroscience Letters 322 (2002), pp. 145-148, Florence, Italy.
Grigoleit et al., Gastrointestinal clinical pharmacology of peppermint oil, Phytomedicine 12 (2005), pp. 607-611, Wiesbaden, Germany.
Hui He, Mingzhang Lin; Zhenhui Han; Yusa, Muroya; Hisaaki, Kudo; Yosuke, Katsumura; The Formation and Properties of the Melatonin Radical; a Photolysis Study of Melatonin With 248 nm Laser Light; Org., Biomol.Chem., 2005, 3, 1568-1574.
International Search Report dated Jan. 29, 2014 for PCT/US2013/000217.
International Search Report dated Aug. 14, 2012 for PCT/US2012/041224.
International Search Report dated Feb. 4, 2014 for PCP/US2013/061146.
International Search Report dated Jun. 21, 2012 for PCT/US2012/22848.
International Search Report dated May 25, 2012 for PCT/US2012/024110.
Japanese Report on Melatonin; 2005.
Juergens et al., The Anti-Inflammatory Activity of L-Menthol Compared to Mint Oil in Human Monocytes in Vitro; A Novel Perspective for its Therapeutic Use in inflammatory Diseases, Eur J. Med Res (1998) 3: 539-545, Dec. 16, 1998.
Kazwini et al., One Electron Oxidation of Methoxylated and Hydroxylated Indoles by N3. 1, Characterization of the Primary Indolic Radicals; J. Phys. Chem, Jan. 25, 1990.
Kellow et al., Altered Small Bowel Motility in Irritable Bowel Syndrome is Corrected with Symptoms, Gastroenterology, 1987, vol. 92, pp. 1885-93, Rochester, Minnesota, USA.
Kline et al., Enteric-Coated pH-dependent peppermint oil capsules for the treatment of irritable bowel syndrom in children, J Pediatr. 2001: 138: 125-8.
Lee et al., Design and evaluation of an oral controlled release delivery system for melatonin in human subjects, InternationalJournal of Pharmaceutics 124 (1995) 119-127, College of Pharmacy, Kangwon National Univeristy Chuncheon. South Korea, Department of Pharmaceutics, College of Pharmacy, Oregeon State Univeristy, Corvallis, OR 97331-3507, USA, Department of Psychiatry School of Medicine Oregon Health Sciences University,Portland, OR, USA.
Lee et al., Formulation and Release Characteristics of Hydroxprophyl Methycellulose Matrix Tablet Containing Melatonin, Drug Development and Industrial Pharmacy, 25(4), 493-501 (1999), Biological Rhythm and Controlled Release Laboratory, College of Pharmacy, Knagwon National Univeristy, Chuncheon 200-709, Korea.
Lee, Beom-Jin; Han-Gon, Choi; Kim, Chong-Kook; Parrott, Keith A.; Ayres, James W,; Sack, Robert L.; "Solubility and Stability of Melatonin in Propylene Glycol and 2-Hydroxpropyl-Beta-Cyclodextrin Vehicles"; Arch. Pharm. Res. vol. 20, No. 6, pp. 560-565; 1997.
Lisa M. Del Valle-Mojica, Jose M. Cordero-Hernandez, Giselle Gonzalez-Medina, Igmeris Ramos-Velez, Nairimer Berrios-Cartagena, Bianca A. Torres-Hernandez, and Jose G. Ortiz; Aqueous and Ethanolic Valeriana Officinalis Extracts Change the Binding of Ligands to Glutamate Receptors; Evidence-Based Complementary and Alternative Medicine, vol., Article ID 891819; 2011.
Liu et al., pH-Responsive amphiphilic hydrogel networks with IPN structure; A strategy for controlled drug release International Journal of Pharmaceutics 308-(2006) 205-209, Department of Applied Chemistry, School of Science Northwestern Polytechnic University, Xi'an 710072, PR China.
M. Goppel, G. Franz; "Stability Control of Valerian Ground Material and Extracts: a New HPLC-Method for the routine Quantification of Valerenic Acids and Lignans:" Department of Pharmaceutical Biology, Institute of Pharmacy, University of Regensburg, Germany; Pharmazie, vol. 59; pp. 446-452; 2004.
MacPherson et al., More than cool; promiscuous relationships of menthol and other sensory compounds, Mol. Cell. Neurosci, vol. 32, 2006, pp. 335-343.
McIntyre et al., Melatonin Rhythm in Human Plasma and Saliva, Journal of Pineal Research 4:177-183 (1987), Psychoendocrine Research Unit, Department of Psychiatry, Austin Hospital Heidelbert (I.M.M., T.R.N., G.D.B.), and Department of Psychology, Brain Behaviour Research Institute, Latrobe University, Bundoora (S.M. A.) Victoria Australia.
Menthols (inchem,org/documents/sids/sids/MENTHOLS.pdf; Last visit Feb. 6, 2014.
Micklefield et al., Effects of Peppermint Oil and Caraway Oil on Gastroduodenal Motility, Phytother, Res., 14, 20-23, 2000.
Pilbrant et al., Development of an oral formulation of omeprazole, Scand J. Gastroenterol, 1985, vol. 20 (suppl. 108, pp. 113-120, Molndal, Sweden.
Pilbrant, Formulation of proton pump inhibitors, Capsugel Library, BAS 153-d.
Pittler et al., Peppermint Oil for Irritable Syndrome; A Critical Review and Metaanalysis, The American Journal of Gastroenterology, vol. 93, No. 7, 1998, 1131-1135.
Product Review: Valerian Supplements; Consumer Lab.com; http://www.consumerlab.com/results/print.asp?reviewid=valerian; Mar. 8, 2016.
Rediger Hardeland; New Approaches in the Management of Insomnia: Weighing the Advantages of Prolonged-Release Melatonin and Synthetic Melatoninergic Agonists; Neuropsychiatric Disease and Treatment; 2009; vol. 5; pp. 341-354.
Rees et al., Treating Irritable Bowel Syndrome with Peppermint Oil, British Medical Journal, Oct. 6, 1979.
Rein Bos, Herman J. Woerdenbag, Henk Hendriks, Jan H. Zwaving, Peter A. G. M. Desmet, Gerolf Tittle, Hakan V. Wikstrom, and Johannes J.C. Scheffer; "Analytical Aspects of Phytotherapeutic Valerian Preparations"; Phytochemical Analysis, vol. 7, pp. 143-151, 1996.
Rohloff et al., Effect of Harvest Time and Drying Method of Biomas Production, Essential Oil Yield and Quality of Peppermint (*Mentha x piperita* L.), J. Agric Food Chem, 2005, vol. 53, pp. 4143-4148 Hedmark, Norway.
Roy Upton; "Valerian Root;" American Herbal Pharmacopoeia, Apr. 1999.
RXMED, Pharmaceutical Information—Copermin, Peppermint Oil Symptomatic Relief of Irritable Bowel Syndrome, Jan. 4, 2010.
Sibanda et al., Experimental Design for the Formulation and Optimization of Hovel Cross-linked oilispheres Develooed for in Vitro Site-Specific Release of Mentha piperita Oil, AAPS PharmSciTech 2004: 5(1) Article 18 (http://www.aapsharmscitech.org, submited Nov. 5, 2003, Accepted Feb. 18, 2004.
Siepe, Stefanie et al. Strategies for the design of hydrophilic matrix tables with controlled microenvironmental pH, International Journal of Pharmaceutics 316 (2006) 14-20.

(56) References Cited

OTHER PUBLICATIONS

Somerville et al., Delayed Release Peppermint Oil Capsules (Colpermin) for the spastic colon syndrome; a phamacokinetic study, Br. J. clin. Pharmac., (1984), vol. 18, pp. 638-640, Ipswich, United Kingdom.

Stevens et al., The short term natural history of irritable bowel syndrome; a time series analysis, Behav. Res Ther., vol. 35, No. 4, pp. 319-326, 1997, Albany, NY, USA.

Tasimelteon Monograph; National Drug Monograph; VA Pharmacy Benefits Management Services, Medical Advisory Panel, and Pharmacist Executives; Nov. 2014.

The Migrating Motor Comples, http://www.vivo.colostate.edu/hbooks/pathphys/digestion/stomach/mmcomplex.html.

Thompson, Shaun, List of Proton Pump Inhibitors,Mar. 12, 2011, http://www.livestrong.com/article/26705-listproton-pump-inhibitors.

Tran et al., New findings onmelatonin absoprtion and alterations by pharmaceutical excipients using the Ussing chamber technique with mounted rat gastrointestinal segments, International Journal of Pharmaceuticals 378 (2009) pp. 9-16, Bioavailability Control Laboratory, College Pharmacy, Kangwon National University, Chuncheon 200-701, Republic of Korea.

Trimble et al., Heightened Visceral Sensation in Functional Gastrointestinal Disease is not site-specific, Digestive Diseases and Sciences, vol. 40, No. 8, Aug. 1995, pp. 1607-1613.

Turek et al., Melatonin Sleep, and Circadian Rhythms; rationale for development of specific melatonin agonists, Sleep Medicine 5 (2004) 523-532.

White et al., A pharmacookinetic comparison of two delayed-release peppermint oil preparations, Colpermin and Mintec, for treatment of the irritable bowel syndrome, International Jounral of Pharmaceutics, vol. 40, 1987, pp. 151-155, Ipswich, United Kingdom.

Yuasa et al., Whisker Growth of L-menthol in coexistence with various excipents, International Journal of Pharmacutics 203, (2000), pp. 203-210, Tokyo, Japan.

International Search Report dated Jul. 26, 2017 for PCT/US2017/031012.

International Search Report dated Jul. 26, 2017 for PCT/US2017/031046.

Lee et al.; "Formulation and Release Characteristics of Hydroxypropyl Methylcellulose Matrix Table Containing Melatonin;" Drug Development and Industrial Pharmacey (online), Apr. 1999, Retrieved from the Internet:<URL: http://www.ncbi.nlm.nih.gov/pubmed/10194604>, retrieved on Apr. 27, 2012.

Office Action for U.S. Appl. No. 15/586,709, dated Jul. 11, 2017.

The International Pharmacopoeia—Sixth Edition, 2016, 1 page.

Shida CS, Castrucci AML, Lamy-Freund MT; "High Melatonin Solubility in Aqueous Medium;" J Pineal Res., vol. 16, pp. 198-201; 1994.

\* cited by examiner

CONTROLLED-RELEASE COMPOSITIONS OF MELATONIN COMBINED WITH SEDATIVE AND/OR ANALGESIC INGREDIENTS

CROSS-REFERENCE TO RELATED APPLICATIONS

This is a divisional of application Ser. No. 15/148,665, filed May 6, 2016, which is a continuation-in-part of application Ser. No. 14/942,299, filed Nov. 16, 2015, which is a division of application Ser. No. 14/186,599, filed Feb. 21, 2014, now U.S. Pat. No. 9,186,351, which is a continuation of application Ser. No. 13/359,638, filed Jan. 27, 2012, now U.S. Pat. No. 8,691,275, which claims priority to provisional Application No. 61/437,217, filed Jan. 28, 2011. Each of these prior applications is incorporated by reference in its entirety.

FIELD

This relates to the field of melatonin compositions and, more particularly, to controlled-release melatonin compositions.

SEQUENCE LISTING

The application contains a Sequence Listing electronically submitted via EFS-web to the United States Patent and Trademark Office as a text file named "Sequence_Listing.txt." The electronically filed Sequence Listing serves as both the paper copy required by 37 C.F.R. § 1.821(c) and the computer readable file required by 37 C.F.R. § 1.821(c). The information contained in the Sequence Listing is incorporated by reference herein in its entirety.

BACKGROUND

Melatonin is a hormone secreted by the pineal gland, a small pinecone-shaped gland located near the center of the brain. Its chemical formula is N-acetyl-5-methoxytryptamine, which is a derivative of the amino acid tryptophan and serotonin. The pineal gland secretes melatonin in a circadian rhythm, which is an approximately 24 hour cycle in the biochemical, physical, or behavioral processes of an organism. A circadian rhythm is an endogenous, or built-in function that is adjusted by environmental stimuli, such as daylight. It is known that the body plasma concentration of melatonin is low during the daytime, starts to rise during the late evening, and is maintained at 25-120 pg/mL during the night (over 8 hours) until it returns to the daytime baseline.

Exogenous, or synthetic melatonin has been proposed to have therapeutic potential in human subjects for treating melatonin deficiency, circadian rhythm disorders, sleep disorders, jet lag, shift work syndrome, and seasonal affective diseases. Some suggest that melatonin may also be effective in the treatment of breast cancer, fibrocystic breast diseases, and colon cancer. Melatonin has been shown to modify the immune response, the stress response, certain aspects of the aging process, sleep disturbances in Alzheimer's patients, and oxidative stress. This suggests a plethora of beneficial uses for melatonin.

Exogenous melatonin treatments suffer from several problems. Melatonin is eliminated from the blood quickly once administered. It has a plasma elimination half-life of less than one hour. When administered orally, it shows low and variable bioavailability. As with most oral administrations, it can take more than 30 minutes after ingestion for the blood plasma concentration of melatonin to reach its peak. This is partly due to the need for release of the melatonin from the dosage form followed by permeation through the wall of the gastrointestinal tract for absorption to occur before the melatonin can enter the bloodstream.

Melatonin is slightly soluble, has good permeability characteristics, and is in the class II category according to the Biopharmaceutics Classification System. Therefore, the amount of melatonin available for absorption into the bloodstream primarily depends on its solubility. Melatonin's solubility generally decreases in less acidic environments. Because the pH of the gastrointestinal tract varies significantly, different amounts of melatonin are available for absorption into the bloodstream, depending on the region of the G.I. tract the melatonin enters.

Orally administered immediate and controlled release melatonin formulations exist. Studies indicate large intersubject variability of melatonin in the blood plasma of human subjects given melatonin orally. Other problems reported include poor oral bioavailability and a nutritional status effect on the oral bioavailability.

Various formulations of melatonin have been developed to provide release of melatonin over a 3 to 10 hour period to stimulate the body's natural release of melatonin. These formulations have not gained wide acceptance because of their variable response in patients. Patients may experience middle of the night awakening, early morning grogginess, and sleep times of less than 5 hours.

Other natural products besides melatonin are often marketed as dietary supplements, but most dietary supplements are only available in a dosage form that releases all of the active ingredients quickly once the dosage form starts dissolving in the body.

BRIEF SUMMARY

In view of the foregoing, it would be advantageous to have a controlled-release dosage form including melatonin in combination with one or more other active ingredients that work in concert with melatonin, such as sedative and/or analgesic ingredients.

A first example of such a composition comprises a pharmaceutical dosage form having a solid core including a combination of melatonin and a GABA receptor agonist ingredient located together within a first acidified polymeric matrix THAT may have a pH of about 1 to about 4.4. An expedited release portion of the dosage form includes 5% to 50% of the GABA receptor agonist ingredient in the dosage form. The expedited release portion is effective to release substantially all of the GABA receptor agonist ingredient therein within about 2 hours from placement in a 0.1 N HCl solution. A sustained release portion of the dosage form includes the remainder of the of GABA receptor agonist ingredient in the dosage form. The sustained release portion is effective to release substantially all of the GABA receptor agonist ingredient therein within about 10 hours from placement in a phosphate buffer with a pH of 6.8.

The sustained release portion may include a plurality of individual granules that have the remainder of the GABA receptor agonist ingredient in the pharmaceutical dosage form therein.

The composition may further comprise an analgesic ingredient in the expedited release portion.

The composition may further comprise an analgesic ingredient in the expedited release portion and the sustained release portion may include a plurality of individual granules that have the remainder of the GABA receptor agonist ingredient in the pharmaceutical dosage form therein.

The GABA receptor agonist ingredient may include valerian and the expedited release portion may further include an analgesic ingredient.

The GABA receptor agonist ingredient may include valerian and the expedited release portion may further include an analgesic ingredient having salicin therein.

The pharmaceutical dosage form may be at least one of a compressed tablet, capsule, and multiparticulate-containing oral dosage form.

In the expedited release portion, the 5% to 50% of the GABA receptor agonist ingredient in the pharmaceutical dosage form may be located within a second acidified polymeric matrix having a pH of about 1 to about 4.4.

A second example of such a composition comprises a pharmaceutical dosage form having a solid core including a combination of melatonin and an analgesic ingredient, the melatonin being located within a first acidified polymeric matrix may have a pH of about 1 to about 4.4. An expedited release portion of the dosage form includes 5% to 50% of the analgesic ingredient and the melatonin in the dosage form. The expedited release portion is effective to release substantially all of the analgesic ingredient and melatonin therein within about 2 hours from placement in a 0.1 N HCl solution. A sustained release portion of the dosage form includes the remainder of the analgesic ingredient and melatonin in the dosage form. The sustained release portion is effective to release substantially all of the analgesic ingredient and melatonin therein within about 10 hours from placement in a phosphate buffer with a pH of 6.8.

The sustained release portion may include a plurality of individual granules that have the remainder of the melatonin in the pharmaceutical dosage form therein.

The composition may further comprise a GABA receptor agonist ingredient in the acidified polymeric matrix.

The analgesic ingredient may include a salicin source. The salicin source may be a white willow bark extract that is at least about 75% salicin.

The pharmaceutical dosage form may be at least one of a compressed tablet, capsule, and multiparticulate-containing oral dosage form.

In the expedited release portion, the 5% to 50% of the analgesic ingredient in the dosage form may be located within a second acidified polymeric matrix having a pH of about 1 to about 4.4.

A third example of such a composition comprises a pharmaceutical dosage form having a solid core including a salicin source and a combination of melatonin and valerian, the melatonin and valerian being located together within a first acidified polymeric matrix may have a pH of about 1 to about 4.4. An expedited release portion of the dosage form includes 5% to 50% of the salicin source, valerian, and melatonin in the dosage form. The expedited release portion is effective to release substantially all of the salicin source, valerian, and melatonin therein within about 2 hours from placement in a 0.1 N HCl solution. A sustained release portion of the dosage form includes the remainder of the of the salicin source, valerian and melatonin in the dosage form. The sustained release portion is effective to release substantially all of the salicin source, valerian, and melatonin therein within about 10 hours from placement in a phosphate buffer with a pH of 6.8.

The salicin source may be a white willow bark extract that is at least about 75% salicin.

The pharmaceutical dosage form may be at least one of a compressed tablet, capsule, and multiparticulate-containing oral dosage form.

In the expedited release portion, the 5% to 50% of the valerian and melatonin in the dosage form is located within a second acidified polymeric matrix having a pH of about 1 to about 4.4.

The sustained release portion may include a plurality of individual granules that have the remainder of the valerian and melatonin in the pharmaceutical dosage form therein.

Any of these example compositions may be employed in a method of treating a patient in need thereof by administering an effective amount of the composition to the patient.

DETAILED DESCRIPTION OF EXAMPLE EMBODIMENTS

Figure 1:
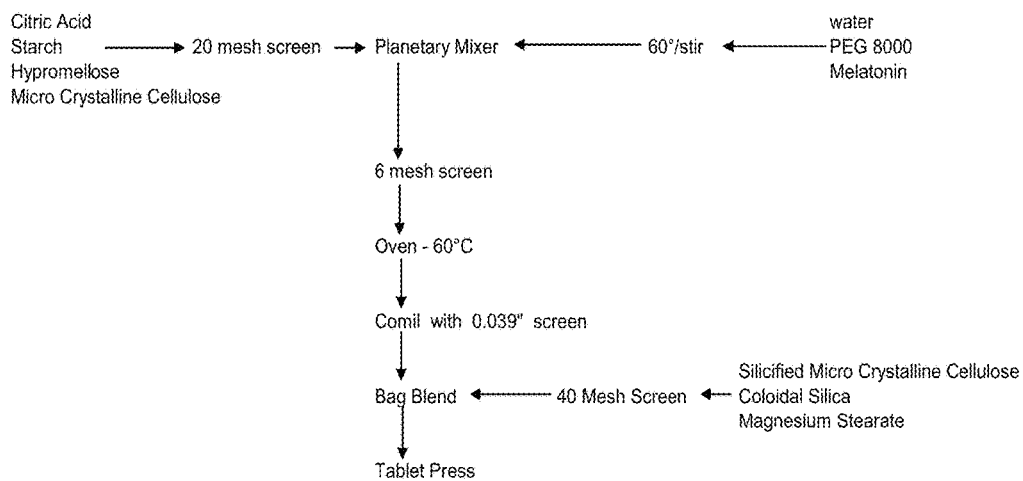
FIG. 1 is a flow diagram illustrating an embodiment of a low shear granulation process.

The melatonin composition may include at least one sedative ingredient in combination with melatonin. Such sedative ingredients may include a skeletal muscle relaxer, and/or a GABA modulator such as a GABA receptor agonist. Examples of sedative ingredients include, but are not limited to, valerian, L-theanine, lemon balm, skullcap, and a decapeptide having the amino acid sequence Tyr-Leu-Gly-Tyr-Leu-Glu-Gln-Leu-Leu-Arg (SEQ ID NO: 1 YLGYLEQLLR), which is marketed as LACTIUM® (Ingredia Societe AnonymeFrance) and described in U.S. Pat. No. 5,846,939.

Melatonin has been reported to have a pKa of approximately 4.4 to 4.7. This gives melatonin different degrees of dissociation and different solubilities as it travels through the GI tract due to pH changes. In the gastric environment, at a pH range of approximately 1 to 3, its solubility is relatively high. In the upper GI tract environment, at a pH range of approximately 4.5 to 5.5, its solubility decreases. In the lower GI tract environment, at a pH range of approximately 5.5 to 7, its solubility decreases even further. This variability in the GI tract pH is not a major factor for conventional immediate-release melatonin dosage forms, as melatonin is readily dissolved in the low pH of the gastric environment. Unfortunately, this results in the melatonin being absorbed and eliminated too quickly to mimic the pattern of the endogenous melatonin found in healthy young subjects.

A first embodiment of the composition includes melatonin in a polymer matrix with the sedative ingredient. In this embodiment it may be desirable to use sufficient acidifying agent to impart a pH of 4.4 or below to the polymer matrix. Examples of such pH ranges include 0.1 to 4.4, 1 to 4.4, 2 to 4.4, 3 to 4.4, 4 to 4.4, 1 to 4, 2 to 4, or 3 to 4. In this pH range the solubility of melatonin is enhanced compared to a neutral pH.

This may be useful for obtaining a sustained release of melatonin throughout the GI tract. Melatonin is much more soluble in the stomach than the intestines because the pH of the stomach is low whereas the pH of the intestines is higher. The acidified polymer matrix forms a controlled pH carrier for the melatonin within the GI tract. Melatonin remains solubilized in the matrix when it absorbs water in the GI tract and can gradually release from the matrix as the dosage form passes through the GI tract, regardless of the GI tract's local pH environment.

The dosage form provides a sustained release of melatonin and the sedative ingredient. Such a product is useful as a sleep aid with dual therapeutic functionality. The sedative ingredient will help the patient relax prior to falling asleep. The melatonin will help the patient fall asleep and stay asleep through the night.

The dosage form is adapted to release an effective amount of sedative ingredient and melatonin within the pH range found in the intestines continuously for at least 3 and up to 10 hours. In a particular example, the dosage form is adapted to release melatonin over a period of 3-10 hours after ingestion regardless of the pH environment it passes through. This sustained release of sedative ingredient and melatonin will help the subject remain asleep through the night.

A second embodiment of the composition includes at least one analgesic ingredient in combination with the sedative ingredient and melatonin. The analgesic ingredient will further provide pain relief.

Examples of analgesic ingredients include, but are not limited to salicin, acetylsalicylic acid, sodium salicylate, acetaminophen, ibuprofen, diclofenac, ketoprofen, bromelain, and naproxen.

In a particular example of the composition, the analgesic ingredient is a salicin source, such as willow bark (*Salix* spp.) or willow bark extract. Salicin is pain relieving anti-inflammatory compound similar in structure to acetylsalicylic, which is the active ingredient in Aspirin. Willow bark may also contain other flavonoids that are analgesic ingredients. Willow bark has been used to treat headaches, muscle pain, and arthritis among many other conditions.

The salicin source may contain willow bark from one or more willow species. There are various types of willow bark that contain salicin, including bark from the white willow (*Salix alba*), black willow (*Salix nigra*), crack willow (*Salix fragilis*), purple willow (*Salix purpurea*), and weeping willow (*Salix babylonica*). The amount of salicin in the willow bark varies amongst species and age of the tree. If white willow bark is the salicin source, it may be desirable to choose a white willow bark extract containing at least 75%, 85%, or 95% salicin.

In the composition, the polymeric matrix effectively insulates the melatonin and sedative ingredient from the pH environment of the GI tract. Instead of dissolving directly into the GI tract, the melatonin and sedative ingredient dissolve within the polymeric matrix, forming a concentration gradient across the matrix. Melatonin and the sedative ingredient will then be released into the GI tract from the periphery of the matrix in this manner.

The polymer matrix is formed from at least one pharmaceutically acceptable polymeric excipient. Examples of polymeric excipients include, but are not limited to: cellulosic polymers such as carboxymethylcelluloses, methylcelluloses, hydroxypropylcelluloses, and hydroxypropylmethylcelluloses; hyaluronates; alginates; polysaccharides, heteropolysaccharides, pectins; poloxamers; poloxamines; ethylene vinyl acetates; polyethylene glycols; dextrans; polyvinylpyrrolidones; chitosans; polyvinylalcohols; propylene glycols; polyvinylacetates; phosphatidylcholines, lecithins; miglyols; polylactic acid; polyhydroxybutyric acid; mixtures thereof, copolymers thereof, derivatives thereof, and the like.

In a particular example, the at least one polymeric excipient is a hydrogel-forming polymer. A hydrogel-forming polymer is a polymer capable of swelling by absorbing water. When ingested by a patient, the hydrogel-forming polymer absorbs water and swells. The active ingredient(s) in the core disperse through the formed hydrogel and gradually exit the hydrogel into the patient's gastrointestinal tract. The hydrogel-forming polymer may act as a release-controlling polymer to provide a sustained release of active ingredient(s) into the GI tract over a desired time period.

Hydroxypropyl methylcellulose ("HPMC" or "hypromellose") is used in certain particular formulations of the dosage form because it forms a hydrogel and is available in many different versions that vary by molecular weight. Thus the properties of the dosage form can be varied by selecting different a different molecular weight version of HPMC.

The acidic pH is imparted to the polymer matrix by blending an acidifying agent such as an acid and/or an acidic buffer with the polymeric excipient. Examples of acidifying agents include, but are not limited to, acidic molecules including organic and/or inorganic acidic molecules. Organic acidic molecules include, but are in no way limited to, low molecular weight carboxylic acids such as citric acid, succinic acid, and tartaric acid. Inorganic acidic molecules include phosphoric acid and hydrochloric acid, for example. Acidic buffers can be prepared with organic or inorganic acidic molecules. Acidic buffers such as mono sodium citrate or mono potassium phosphoric acid (monopotassium phosphate) are examples, but acidic buffers are in no way limited to these.

The pharmaceutical dosage form will typically be an oral dosage form such as a tablet, caplet, capsule, multiparticulate, or the like. In such cases, the dosage form has a solid core containing one or more of the active ingredients within the polymer matrix.

The amount of acidifying agent is sufficient to impart an acidic pH to the polymer matrix when it absorbs water and swells. Some suitable approximate pH ranges for the polymer matrix include 0.1 to 7, 0.1 to 6, 0.1 to 5, 1 to 6, 1 to 5, 2 to 6, 2 to 5, 2.5 to 5.5, 2 to 4.5, 3 to 6, 3 to 5, 3 to 4.5, 3.3 to 5, or 3.4 to 4.5.

In the products discussed above the dosage form includes a sustained release portion, which is the polymer matrix containing the active ingredient(s). The sustained release portion is effective to release the active ingredient(s) therefrom into the patient's lower GI tract over about 3 hours to about 10 hours after oral ingestion by the patient. In certain cases, the dosage form will release substantially all of the active ingredient(s) therefrom within 10 hours after oral ingestion or within about 8 hours after oral ingestion.

The dosage form may also include an expedited release portion. The expedited release portion is effective to release about 50% of the active ingredient(s) into the lower GI tract within about 2 hours after oral ingestion or about 1 hour after oral ingestion.

The expedited release portion of the dosage form can be formulated many different ways. A few examples are described below, but these examples are not an exhaustive list of the many possibilities.

The polymer matrix may function as both the expedited release portion and sustained release portion. This is because when the dosage form reaches the patient's stomach, it will begin releasing some of the active ingredients from the polymer matrix almost immediately as the polymer matrix absorbs water in the stomach. As the polymer matrix swells, a pH gradient forms within the matrix and the release rate of the active ingredients slows.

Another example of a dosage form with an expedited release portion and sustained release portion is a bi-layer tablet having one layer forming the sustained release portion and another layer forming the expedited release portion.

Another example of a dosage form with an expedited release portion and sustained release portion is a capsule containing the sustained release portion and expedited release portion. In such an example, the expedited release portion may include particulates effective to release the active ingredients therein over a desired expedited time period and the sustained release portion may be another set of particulates effective to release the active ingredients therein for a sustained time period.

Another example of a dosage form with an expedited release portion and sustained release portion is a tablet or capsule in which the polymer matrix forms a solid core and the expedited release portion is in a coating over the core.

The relative dosage percentage of the expedited and sustained release portions can vary. In some examples, the expedited release portion contains 5% to 50% or up to 65% of a particular active ingredient in the dosage form. In other examples, the sustained release portion contains up to 90% of a particular active ingredient in the dosage form. In another example, the expedited release portion contains approximately 50% of the active ingredient(s). The active ingredients from the expedited release portion are released approximately in the first two hours after ingestion. The active ingredients in the sustained release portion include the remainder of the active ingredient(s), which are released approximately over the next 5-8 hours or within about 10 hours after ingestion.

The release profile may be measured by simulating the GI tract environment by placing the dosage form in a 0.1 N HCl (hydrochloric acid) solution for two hours, then placing it in a phosphate buffer solution of pH=6.8 for 12 hours.

The release rate of the active ingredient(s) from the dosage form can be controlled in several ways. The concentration of the active ingredient(s) may be adjusted. The pH of polymer matrix may be adjusted. One or more release rate controlling coatings may be included. The thickness of such a coating may be adjusted. The size and shape of the dosage form may also be adjusted to provide the preferred release rate.

An effective amount is an amount that is sufficient to provide a therapeutic benefit affecting a disease or condition in the body.

A therapeutically effective amount of sedative ingredient, melatonin, and/or analgesic ingredient may be 1-1,000 mg/day, including 1-25 mg/day, 25-50 mg/day, 50-75 mg/day, 75-100 mg/day, 100-150 mg/day, 150-200 mg/day, 200-250 mg/day, 250-300 mg/day, 300-350 mg/day, 350-400 mg/day, 400-450 mg/day, 450-500 mg/day, 500-550 mg/day, 550-600 mg/day, 600-650 mg/day, 650-700 mg/day, 700-750 mg/day, 750-800 mg/day, 800-850 mg/day, 850-900 mg/day, 900-950 mg/day, 950-1,000 mg/day. Higher doses (1,000-3,000 mg/day) might also be effective. The weight in mg is often calibrated to the body weight of the patient in kg, thus these example doses may also be written in terms of mg/kg of body weight per day.

If the dosage form includes L-theanine, an effective amount of L-theanine may be 25-250 mg, 50-200 mg, or about 100 mg may be used.

If the dosage form includes skullcap, an effective amount of skullcap may be 25-250 mg, 50-200 mg, or about 100 mg may be used.

If the dosage form includes lemon balm, an effective amount of lemon balm may be 25-250 mg, 50-200 mg, or about 100 mg may be used.

If the dosage form includes the decapeptide, an effective amount of the decapeptide may be 25-250 mg, 50-200 mg, or about 100 mg may be used.

In practice, the therapeutically effective amount may vary depending on numerous factors associated with the patient, including age, weight, height, severity of the condition, administration technique, and other factors. The therapeutically effective amount administered to a patient may be determined by medical personnel taking into account the relevant circumstances.

The therapeutically effective amount may be determined or predicted from empirical evidence. Specific dosages may vary according to numerous factors and may be initially determined on the basis of experimentation.

The product may be administered as a single dose or as part of a dosage regimen. For a dosage regimen, the therapeutically effective amount is adjustable dose to dose to provide a desired therapeutic response.

Multiple doses may be administered at a predetermined time interval and subsequent doses may be proportionally reduced or increased, depending on the situation.

Table 1 is a list of a few of the possible therapeutically effective amounts of active ingredients in several examples of the composition, Examples A-H. Here, the mass is reported by weight of a unitary dosage form. This list is not meant to be exhaustive.

TABLE 1

Amounts of active ingredient(s) in examples of the composition.

| Active | Mass (milligrams) | | | | | | | |
| --- | --- | --- | --- | --- | --- | --- | --- | --- |
|  | A | B | C | D | E | F | G | H |
| sedative | 100-400 | 150-300 | 100-400 | 150-300 | 100-400 | 150-300 | 150-250 | 190-210 |
| Melatonin | 0 | 0 | 1-10 | 3-6 | 1-10 | 3-7 | 4-6 | 4-6 |
| analgesic | 0 | 0 | 0 | 0 | 150-550 | 200-300 | 240-270 | 250-275 |

Several particular examples of the composition will now be described. The scope of possible embodiments, however, is not limited to these examples. These examples are presented as percent by weight (% w/w) of the specified ingredient relative to the dosage form. If a coating is placed over the dosage form, the % w/w is the pre-coating % w/w. Any combination of the ingredients in the % w/w listed below may be employed.

Melatonin may be 0.1%-5% w/w; 0.1%-2% w/w, 0.1% to 1% w/w, or 0.2%-0.7% w/w.

The sedative ingredient may be 10%-50% w/w, 15%-45% w/w, 15%-40% w/w, 15%-35% w/w, 15%-25% w/w, 18%-24% w/w, or 20%-22% w/w.

The polymer excipient may be 0.5%-20% w/w, 1%-20% w/w, 1%-15% w/w, 1%-7% w/w, 1%-5% w/w, 2%-6% w/w, or 2%-4% w/w.

The acidifying agent may be 0.5%-20% w/w, 1%-20% w/w, 1%-15% w/w, 5%-15% w/w, 2%-10% w/w, 7%-15% w/w, 6%-10% w/w, or 7%-9% w/w.

The binder may be 0.5%-20% w/w, 2%-15% w/w, 9%-33% w/w, 10%-20% w/w, 12%-20% w/w, 12%-18% w/w, or 15%-17% w/w.

The analgesic ingredient may be 15%-60% w/w, 15%-50% w/w, 20%-60% w/w, 20%-55% w/w, 25%-35% w/w, or 26%-30% w/w.

A more particular example of the composition includes: about 15% to about 45% w/w of sedative ingredient; about 0.1% to about 2% w/w melatonin; about 1% to about 15% w/w of acidifying agent; about 1% to about 15% w/w of hydrogel-forming polymer; and about 10% to about 20% binder.

Another more particular example of the composition includes: about 15% to about 45% w/w of sedative ingredient; about 0.1% to about 2% w/w melatonin; about 20% w/w to about 55% w/w salicin source; about 1% to about 15% w/w of acidifying agent; about 1% to about 15% w/w of hydrogel-forming polymer; and about 10% to about 20% binder.

The expedited and sustained release portions may be formulated separately then combined into the final dosage form. For example, the sustained release portion can be formed from a plurality of individual granular particulates that contain the acidified polymeric matrix and active ingredients. Likewise the expedited release portion can be formed from a plurality of individual granular particulates that contain its active ingredients. If melatonin and/or a GABA receptor agonist is included in the expedited release portion, the expedited release portion may also include an acidified polymeric matrix.

In another example, the composition includes a pharmaceutical dosage form that has a solid core including a combination of melatonin and a GABA receptor agonist ingredient located together within a first acidified polymeric matrix having a pH of 1 to 4.4. An expedited release portion of the dosage form includes 5% to 50% of the GABA receptor agonist ingredient in the dosage form. The expedited release portion is effective to release substantially all of the GABA receptor agonist ingredient therein within about 2 hours from placement in a 0.1 N HCl solution. A sustained release portion of the dosage form includes the remainder of the of GABA receptor agonist ingredient in the pharmaceutical dosage form. The sustained release portion is effective to release substantially all of the GABA receptor agonist ingredient therein within about 10 hours from placement in a phosphate buffer with a pH of 6.8.

In another example, the composition includes a pharmaceutical dosage form that has a solid core including a combination of melatonin and an analgesic ingredient. The melatonin is located within a first acidified polymeric matrix having pH of 1 to 4.4 An expedited release portion of the dosage form includes 5% to 50% of the analgesic ingredient and the melatonin in the dosage form. The expedited release portion is effective to release substantially all of the analgesic ingredient and melatonin therein within about 2 hours from placement in a 0.1 N HCl solution. A sustained release portion of the dosage form includes the remainder of the analgesic ingredient and melatonin in the dosage form. The sustained release portion is effective to release substantially all of the analgesic ingredient and melatonin therein within about 10 hours from placement in a phosphate buffer with a pH of 6.8.

In another example the composition includes a pharmaceutical dosage form having a solid core that includes a salicin source and a combination of melatonin and valerian. The melatonin and valerian are located together within a first acidified polymeric matrix having a pH of 1 to 4.4. An expedited release portion of the dosage form includes 5% to 50% of the salicin source, valerian, and melatonin in the dosage form. The expedited release portion is effective to release substantially all of the salicin source, valerian, and melatonin therein within about 2 hours from placement in a 0.1 N HCl solution. A sustained release portion of the dosage form includes the remainder of the of the salicin source, valerian and melatonin in the dosage form. The sustained release portion is effective to release substantially all of the salicin source, valerian, and melatonin therein within about 10 hours from placement in a phosphate buffer with a pH of 6.8.

As mentioned above, the dosage form will typically be an oral dosage form such as a tablet, caplet, capsule, multiparticulate, or the like. One or more pharmaceutically acceptable excipients aside from those described already may be used to obtain the desired dosage form and give it the desired properties.

Examples of excipients include, but are not limited to, carriers, diluents, disintegrants, emulsifiers, solvents, processing aids, buffering agents, colorants, flavorings, solvents, coating agents, binders, carriers, glidants, lubricants, granulating agents, gelling agents, polishing agents, suspending agent, sweetening agent, anti-adherents, preservatives, emulsifiers, antioxidants, plasticizers, surfactants, viscosity agents, enteric agents, wetting agents, thickening agents, stabilizing agents, solubilizing agents, bioadhesives, film forming agents, emollients, dissolution enhancers, dispersing agents, or combinations thereof.

Tablets and caplets may be prepared using conventional tableting techniques such as dry blending or wet granulation. The dry blend or granulation may be compressed into a final tablet form.

Capsules may be prepared using different techniques. For example, dried granules produced by wet granulating the ingredients may be loaded into a capsule, such as a gelatin capsule.

A spray granulation process may be used to prepare the dosage form as well. The spray granulation process produces granular cores containing the active ingredients, the polymer matrix, and the acidifying agent. The granular cores may be combined into a final dosage form such as by compressing them into a tablet or loading them into a capsule, for example.

Alternatively, the capsules may be loaded with individual spheroidal multiparticulates having a diameter of from about 0.5 mm to about 4 mm or from about 0.5 mm to about 3 mm that are prepared by forming a wet mass of the ingredients, extruding the wet mass, cutting the extruded wet mass into pieces, and spheronizing the pieces. The individual particulates may include any of the coatings discussed here.

When preparing the dosage form, it may be desirable to include a solubilizing agent to help solubilize the melatonin. Solubilizing agents include, but are not limited to, polyethylene glycol (PEG) based surfactants. The molecular weight of PEG can be chosen to provide the desired properties of the composition. A solubilizing agent may not be needed in every embodiment of the dosage form.

Conventional processing aids may be used to prepare dosage form. Examples of processing aids include, but are not limited to, magnesium stearate, stearic acid, talc, and sodium lauryl sulfate.

The dosage form may include a pharmaceutically acceptable filler. Examples of fillers include, but are not limited to, silicates, calcium carbonate, glycine, dextrin, sucrose, sorbitol, dicalcium phosphate, calcium sulfate, lactose, kaolin, mannitol, sodium chloride, talc, dry starches and powdered sugar.

The dosage form may include a pharmaceutically acceptable binder. Examples of binders include, but are not limited to, cellulosic, and povidone binders such as microcrystalline cellulose and crospovidone.

Examples of dispersing agents include, but are not limited to, copolymer systems such as polyethylene glycol-polylactic acid (PEG-PLA), polyethylene glycol-polyhydroxybutyric acid (PEG-PHB), polyvinylpyrrolidone-polyvinylalcohol (PVP-PVA), and derivatized copolymers such as copolymers of N-vinyl purine or pyrimidine derivatives and N-vinylpyrrolidone.

The dosage form may be coated to aid in swallowing, to mask the taste of the ingredients, improve appearance, to protect the dosage form from moisture, and/or to have an enteric coating. The coating may be applied using conventional coating techniques, such as, for example, spray coating, bed coating, or the like.

The dosage form may be coated with an enteric coating to substantially prevent the active ingredients from releasing into the stomach. Examples of enteric coating materials include shellac, cellulose acetate phthalate, polyvinyl acetate phthalate, ethyl cellulose/sodium alginate, hypromellose acetate succinate, or a methacrylic acid-based polymer or co-polymer such as methacrylic acid-ethyl acrylate copolymer.

The dosage form may be coated with a seal coating. Examples of seal coating materials include, but are not limited to, hydroxypropyl cellulose, hypromellose, and polyvinyl alcohol. A particular example of the seal coating is OPADRY® Clear (Colorcon, Inc.), which contains, HPMC and polyethylene glycol.

More particular examples of the composition in which valerian is the sedative ingredient are now described. The term "valerian" as used herein includes valerian root, valerian extracts, and the therapeutically active compounds in valerian such as valerenic acid and/or valepotriates such as valtrate and didrovaltrate. Valerian may be in a dried root, powder, or liquid form. The liquid form contains the active components of the valerian root suspended in a solvent. Alcohols are typically used as the extraction solvent, but the liquid form may also be an oil.

In conventional aqueous or hydroalcoholic extracts or tinctures of valerian, the primary water-soluble active compound has been reported to be isovaleric acid. Ammonium isovalerate and isovaleramide are produced in ammoniated tinctures. Valepotriates and monoterpene isovalerate esters, such as bornyl and lavandulyl isovalerates, are reported to act as prodrugs for isovaleric acid, its salts, and isovaleramide.

An embodiment of the valerian-containing composition includes a valerian-containing pharmaceutical dosage form in which valerian is in the polymer matrix with an acidic pH. The acidic pH helps stabilize some of the bio-active compounds in valerian to enhance the storage stability of the valerian-containing composition.

The pKa of valerenic acid and valproic acid is reported to be about 5. In some examples of the composition, it is desirable to use sufficient acidifying agent to impart a pH of 5 or below in order to maintain valerenic acid and valproic acid their protonated forms. It is believed that imparting such a pH to the polymer matrix will help prevent oxidative degradation to these acids.

Although not intended to be bound by theory, it is believed that one of the valerian degradation pathways is decarboxylation of the carboxylic acids such as valerenic acid. Using a carboxylic acid-based acidifying agent may help mitigate decarboxylation. Because decarboxylation may become favorable at elevated temperatures, it is believed that a carboxylic acid-based acidifying agent may improve the storage stability of valerian.

Valerian has been reported to have both a foul smell and taste. If desired, the dosage form may include a taste and/or smell-masking coating.

Valerian also contains volatile components, which may evaporate and leave the dosage form during storage. An evaporation-preventative coating may be applied over the core to minimize evaporation of these components. An example of such an evaporation-preventative coating is a gelatin coating. In some cases, acid bone gelatin may be a desirable source of gelatin.

The polymeric matrix may function to prevent oxidative degradation of valerian. It provides a moisture and oxygen barrier during storage, which substantially prevents moisture and oxygen from penetrating into the dosage form.

The composition in any of the forms described above may be used to treat one or more conditions such as pain, insomnia, anxiety, melatonin deficiency, a sleep disorder, and/or a circadian rhythm disorder.

A patient in need of treatment may be treated by administering the composition described above to the patient. The product may be administered orally. The patient may be a human or animal patient.

EXAMPLES

This section describes a few specific examples of the composition. These examples are presented by way of example only and are not intended to limit the scope of the invention.

Example 1

Tablet Melatonin Composition

A. Experimental Details.

Melatonin (Nutri-Force, lot number 81120) was used in the following experiments. The melatonin was reported to be a micronized grade. Shipment, handling and processing of melatonin and prototypes were all under ambient room temperature. In-process materials and bulk tablets were stored in double polyethylene bags with desiccant. Melatonin was evaluated for appearance and particle size by sieve analysis.

Melatonin was visually characterized as a white to off-white poor flowing, fine powder. The particle size sieve analysis of melatonin revealed a non-Guassian distribution of particles predominately of 150 microns. Manufacture of the melatonin controlled-release tablets dissolves the melatonin in a solution of polyethylene glycol and water as part of the granulation fluid. Therefore, the particle size of the melatonin has no substantial effect on the final properties of the tablet, but did influence the rate at which the melatonin was dissolved during manufacture.

The following equipment was used preparing the formulations: Kitchen Aide planetary mixer; hot plate/magnetic stirrer; #6, 20 and 40 mesh sieves; tray drying oven; comil with 0.039" round hole screen; Piccola B/D 8 station R&D press 0.455"×0.190" capsule shaped tooling; Computrac LOD instrument; tablet hardness tester; tablet friability tester; and calipers.

B. Development of 2 mg Melatonin Controlled-Release Tablets.

This section describes the development of prototype tablets in accordance with the invention. A hypromellose based monolithic tablet was utilized to achieve the targeted 6-8 hours extended release of the 2 mg melatonin. The formulation was varied as presented in Table 1 to identify a formulation with the targeted release profile. The tablet size was held constant throughout the experimentation at 250 mg with a strength of 2 mg melatonin per tablet. The formulations were prepared in small 200-300 g batches.

It was discovered that hypromellose exhibited undesirable flow characteristics. For this reason, a granulation process was used. The prototypes were manufactured using a low shear wet granulation process in a planetary mixer. The intra-granular components were charged to the mixing bowl and granulated either with water in the early prototypes or a solution of water, polyethylene glycol and melatonin in the later prototypes. The wet granulation was wet milled through a 6 mesh hand sieve to break up any large agglomerates and then oven tray dried at 60° C. to a ~1-3% moisture level. The dried granulations were milled to size with a Comil cone type mill using a 0.55" screen initially and later a 0.039" screen. The extra-granular excipients were bag blended into the milled granulation and the final blend was compressed on a Piccola tablet press using 0.455"×0.190" capsule shaped tooling to a tablet weight of 250 mg and hardness of ~5 kp. The process used for the lead prototype lot CYV45-002-048A is summarized in the flow diagram of FIG. 1.

Analysis of Prototypes.

A two stage dissolution procedure in a USP dissolution apparatus type III with 2 hour in 0.1 N hydrochloric acid followed by 12 hours in pH 6.8 phosphate buffer was used to evaluate the prototypes. This was later simplified to a single stage procedure in 0.9% saline when the two methods were shown to give equivalent results. Melatonin assay and related substance testing was performed by HPLC on the identified lead prototype, which was CYV45-002-48A.

Figure 2:
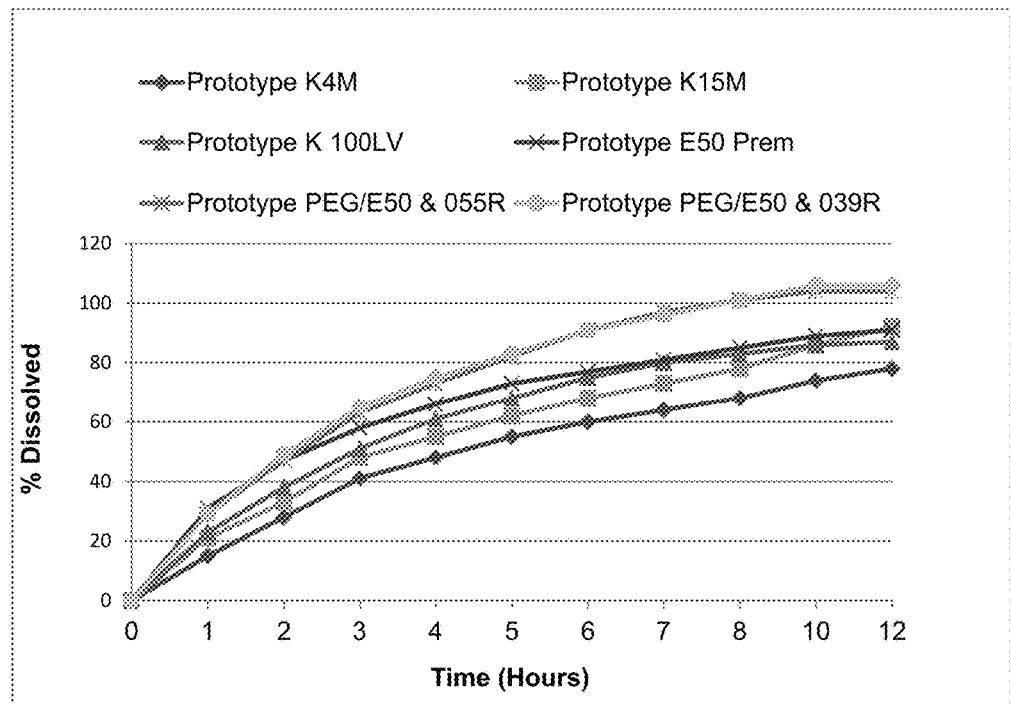
FIG. 2 is a graph of the dissolution profile of examples of melatonin compositions of the invention.

Four different matrix forming hypromellose grades of varying molecular weight (K4M, K15M, K100LV and E50) were initially screened (Lots CYV45-002-004, 007, 011 and 012) as presented in Table 1. The hypromellose E50 hypromellose proved to be the most promising of the polymers evaluated, but it still released the melatonin slower than desired. The dissolution results are presented in FIG. 2.

Citric acid was first included in the formulation at a concentration of 16% but was increased to approximately 30% to maintain a low pH in the tablet matrix, enhancing the aqueous solubility of the melatonin. STARCAP® 1500 (BPSI Holdings, LLC) starch was initially added at a concentration 28% but was reduced to 12% to make room for the added citric acid without increasing tablet size.

The aqueous solubility of the melatonin was further increased, by dissolving the melatonin in a 50% solution of polyethylene glycol surfactant (PEG 3350) and spraying the solution into the granulation. The use of the PEG 3350 successfully increased the dissolution rate.

Concurrently, the effect of granulation particle size on the dissolution was evaluated by using a Quadro Comil with either a 0.055" or 0.039" round hole screen (lot CYV45-002-021A and B). The particle size of the granulation had little effect on dissolution rate but the smaller particle size granules was observed to generate less inter-tablet variability in the dissolution data. As a result, the use of the 0.039" screen was adopted for use in subsequent trials.

It was discovered that compression of the tablets with the PEG 3350 was not ideal. Sticking in the cups of the tablet punches was noted causing cosmetic defects, erratic tablet weight and hardness. To alleviate the sticking problem, higher molecular weight PEG 8000 was substituted for the use of the PEG 3350 in the formulation (lot CYV45-002-030).

Figure 3:
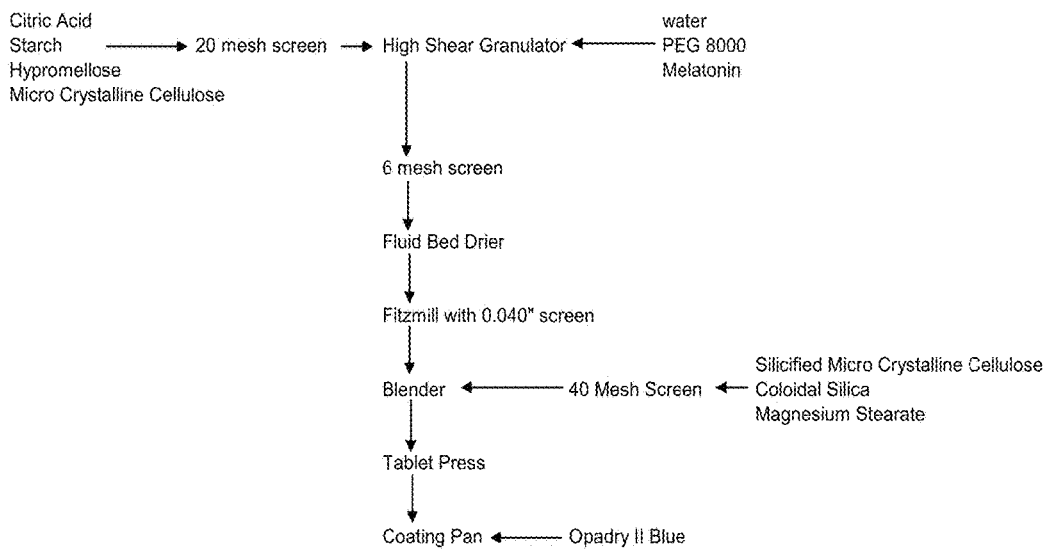
FIG. 3 is a flow diagram illustrating an example of a high shear granulation process for the manufacture of extended-release melatonin tablets.

The batch was also scaled up to a 1 kg size and processed using a high shear granulator and fluid bed in place of the low shear planetary mixer and tray drying oven used previously. This was done to provide ample material to compress for an extended period to investigate the tablet sticking issue and adapt the process to be more suitable for future manufacturing. The scaled up process is summarized in the flow chart of FIG. 3. The equipment used in the scaled up process included the following: Fielder PP1 High Shear granulator; Niro-Aeromatic MP-1 Multi-processor; Fitzmill J mill equipped with a 0.040 round hole screen; 2 Qt PK Blender; Piccola Eight Station B/D tablet press; 0.1920"× 0.4570" capsule shape tooling embossed with "REM" embossed in upper punch; Accela-cota model 24MK III (24" coating pan; hot plate; Overhead mechanical lab stirrer and propeller; and 20 mesh, 6 mesh and 40 mesh sieves.

The tablets were also film coated with an OPADRY® II Blue non-functional coating to simulate the eventual final product that was desired. The granulation, blend and tablets processed well at the increased scale using the high shear granulation process. The sticking problem during tablet compression was alleviated. Coating was conducted successfully with no difficulties. It was discovered that melatonin dissolution was undesirably retarded by the substitution of PEG 8000 for PEG 3350. Accordingly, the formulation was tweaked to optimize the melatonin dissolution.

Figure 4:
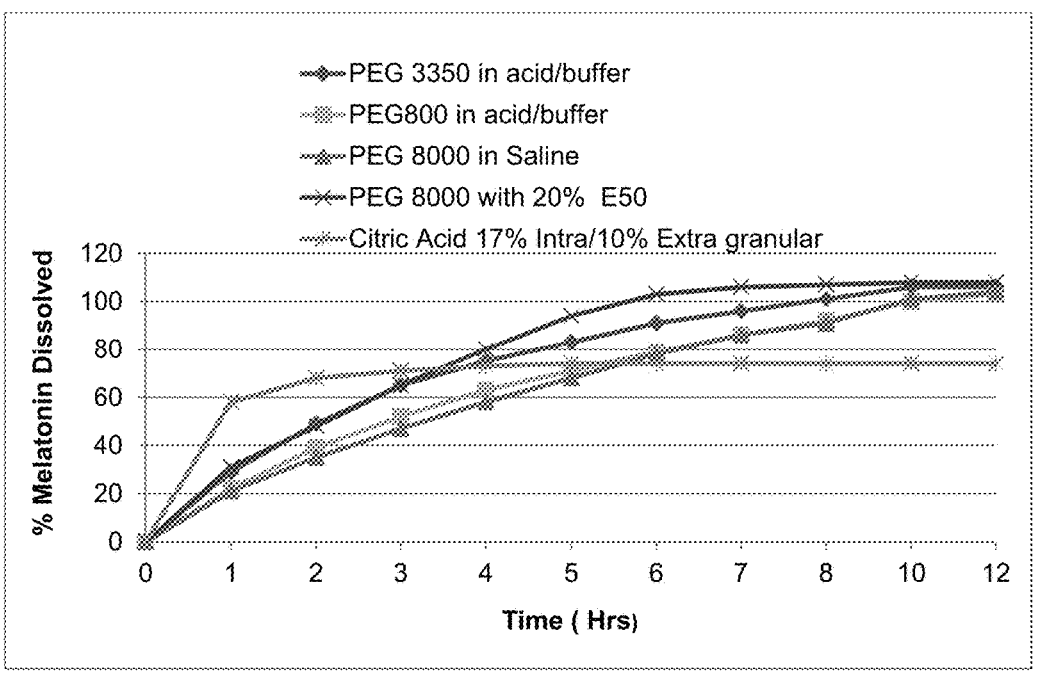
FIG. 4 is a graph of the dissolution profile of an example of an extended-release melatonin tablet.

To compensate for the slower release of melatonin, a small trial formulation with PEG 8000 (lot CYV45-002-048B) was made shifting a portion of the intra-granular citric acid to extra-granular to increase dissolution by increasing the porosity of the tablet matrix. Also, a small trial batch (lot CYV45-002-048A) utilizing the PEG 8000 but reducing the concentration of the matrix forming polymer hypromellose E50 from 30% to 20% was made and evaluated. The tablet weight was held constant by adding additional extra-granular ProSolv which also increased the hydrophilicity of the tablet to accelerate the release of the melatonin. Both approaches increased dissolution rate. Lot CYV45-002-048A with reduced level of E50 (20%) best fit the target dissolution profile (FIG. 4). Table 2 lists the ingredients in this formulation.

Figure 5:
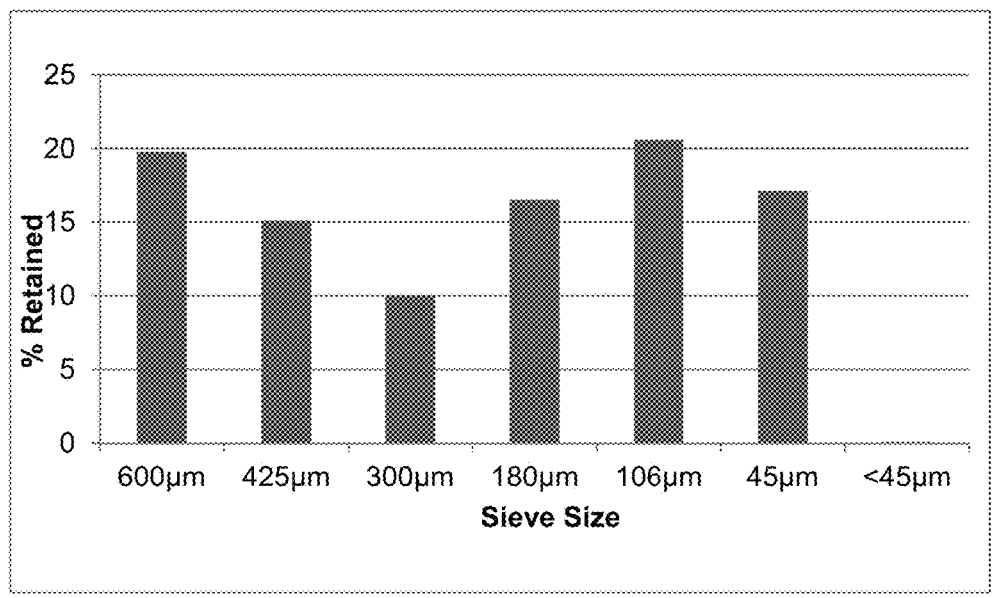
FIG. 5 is a graph of the particle size distribution of an example of a high shear granulated melatonin placebo blend.

The physical properties of the final blend and compressed tablets for the CYV45-002-048A prototype are presented in Tables 3 and 4 and FIG. 5. The particle size of the final blend is non-Guassian and somewhat bi-modal. The flow of the final blend was acceptable as indicated by a blend compressibility of 14% and Flodex critical orifice value of 16 mm. The formulation is preferably compressed with tablet presses utilizing a paddle feeder to ensure good flow and ensure that particle size segregation does not occur in the press feed frame.

The compressed tablets had low tablet weight variation. Tablet hardness and thickness also exhibited low variability. The mean tablet hardness was 3.9 kp with a range of 3.4-4.2 kp. At first glance, this would appear to be low tablet hardness; however, this provided a robust tablet with extremely low friability (0.03% lost in 100 drops) suitable for coating in a tablet coating pan. Because the tablets comprised both PEG and citric acid, the tablets were soft due to plastic deformation; however, this softness is advantageous as it imparts a high degree of impact resistance. The capsule-type shape of the tablets itself with a low cross-sectional area generates deceptively low tablet hardness values.

Prototype Lot CYV45-002-048A was assayed for melatonin and related substances and the results are presented in Table 5. The high assay value of 105.2% can largely be explained as a result of loss of moisture during the granulation drying process. The excipients and melatonin prior to granulation contained 5.1% moisture as determined in a baseline loss on drying evaluation but only contained 1.2% after the granulation was dried; thereby, making the granulation 3.9% super-potent. The granulation moisture will preferably be dried to level approximate to the baseline moisture in future batches.

Because maintaining a low pH in the tablet matrix over the course of the release was a desired property, tablets of CYV45-002-048A were placed in dissolution baths containing saline for up to 7 hours at 50 rpm paddle speed. The "ghost" cores remaining after 7 hours were decanted away and pH of the tablet cores was determined. At 4 hrs the pH was determined to be 2.5 and at 7 hrs it was 2.8. This indicates that citric acid remained in the tablet for an extended period of time to lower the pH and assist in the solubilization of the melatonin.

Preparation of Final Tablet.

The formulation development activities successfully identified a controlled-release prototype for 2 mg dose strength melatonin tablet. The in-vitro dissolution release profile met the desired objective of releasing half the melatonin with 1-2 hours followed by first order release with greater than 90% release achieved at 6 hours. The release of melatonin was shown to be independent of the pH of the dissolution media with similar profiles generated using an acid/pH 6.8 two stage dissolution versus a single stage saline method. The in-vitro dissolution data suggests the tablets will release melatonin quickly to induce sleep and maintain a level of melatonin for up to 6 hours with little melatonin remaining to create grogginess upon awakening. The formulation utilizes GRAS excipients and can be manufactured by a high shear wet granulation process suitable for manufacture in a production facility.

Using the experimental results described above, a final tablet comprising melatonin was prepared. The final tablet comprises the ingredients shown in Table 6 and was prepared according to the procedure that will now be described.

A granulation solution was first prepared by:
(a) charging 58.0 g of purified water to a beaker and heating to approximately 60° C.;
(b) stirring and dissolving 50.0 g of PEG 8000 in the solution of (a);
(c) dissolving 8.0 g of melatonin in the solution of (b), resulting in a clear amber solution; and
(d) allowing the solution of (c) to cool to room temperature.

High shear wet granulation and wet milling was next performed by:
(a) screening the microcrystalline cellulose, citric acid and hypromellose through a 20 mesh sieve and charge to a Niro PP-1 high shear granulator;
(b) mixing the materials in the granulator for approximately three minutes at a speed of 300 rpm;
(c) continued mixing and sprayed the granulation solution on the mixing materials over the course of about 3 minutes;
(d) while continuing mixing, spraying and additional 157 g of water over the course of approximately 5 minutes;
(e) wet massing the granulation by mixing and additional 2-3 minutes; and
(f) discharging the product of (e) from the granulator and sizing the granulation through a 0.156" square hole screen using a Quadro Comil.

Drying granulation and dry milling was next performed by:
(a) charging the wet milled granulation to a Niro MP-1 fluid bed dryer and drying at an air inlet temperature of 60° C.;
(b) drying the product of (a) to approximately 2% moisture content (as determined by an LOD loss on drying instrument—the drying time was approximately 25 minutes);
(c) passing the product of (b) through a Fitzmill J mill at a slow speed in the knives forward mode using a 0.040" round hole screen.

Final blending was achieved by:
(a) charging the dried milled granulation to a 2 quart V-blender;
(b) screening the Cabosil colloidal silicon dioxide through a 20 mesh sieve and charging to the blender;
(c) blending the product of (b) for 120 revolutions;
(d) screening the magnesium stearate through a 40 mesh sieve and charging to the blender; and
(e) blending the product of (d) for 72 revolutions.

The final blend was compressed into a tablet by:
(a) equipping a Piccola BD 8 station rotary tablet press with 0.1920"×0.0.4570" capsule shaped tablet tooling;
(b) loading the tablet press with the final blend; and
(c) compressing tablets to the following targets: tablet weight=250 mg, tablet hardness=8 kp, tablet thickness=0.185."

TABLE 1

Formulations of 2 mg Melatonin Extended Release Tablet Development Prototypes

| | | % w/w Lot # CYV45-002- | | | | | | | |
|---|---|---|---|---|---|---|---|---|---|
| | Ingredient | 004 | 007 | 011 | 012 | 21A/B | 030 | 48A | 48B |
| Intra-granular Components | Melatonin (2 mg/tablet) | | | | | | 0.8 | | |
| | Hypromellose K4M | 30 | | | | | | | |
| | Hypromellose 15M | | 30 | | | | | | |
| | Hypromellose K100LV | | | 30 | | | | | |

TABLE 1-continued

Formulations of 2 mg Melatonin Extended Release Tablet Development Prototypes

| | | % w/w Lot # CYV45-002- | | | | | | | |
|---|---|---|---|---|---|---|---|---|---|
| | Ingredient | 004 | 007 | 011 | 012 | 21A/B | 030 | 48A | 48B |
| | Hypromellose E50 | | | | 30 | 30 | 30 | 20 | 30 |
| | PEG 3350 | | | | | 5 | | | |
| | PEG 8000 | | | | | | 5 | 5 | 5 |
| | Citric Acid | 16 | 16 | 32 | 32 | 27 | 27 | 27 | 17 |
| | Starch | 28 | 28 | 12 | 12 | 12 | 12 | 12 | 12 |
| | MCC | | | | | 12.2 | | | |
| Extra-granular Components | PROSOLV ® HD90 | 12 | 12 | 12 | 12 | 12 | 12 | 22 | 12 |
| | Citric acid | | | | | | | | 10 |
| | CAB-O-SIL ® | | | | | 0.5 | | | |
| | Mag Stearate | | | | | 0.5 | | | |
| | Total | | | | | 100% | | | |

TABLE 2

Quantitative Formula for Melatonin 2 mg ER Tablets Lead Prototype Lot # 11216-048A

| | Materials Vendor/Lot # | Functionality | 2 mg Tablet | % w/w | g/Batch |
|---|---|---|---|---|---|
| Gran. Soln | Melatonin (Nutri-Force lot # 81120) | melatonin | 2.0 | 0.8 | 2.4 |
| | Purified Water[1] | Granulation solvent | NA | NA | 15 g for PEG solution + 33.5 g for granulation |
| | Polyethylene Glycol PEG8000 (Dow) | Solubilizer | 12.5 | 5.0 | 15 |
| Intragranular | Microcrystalline Cellulose, NF AVICEL ® PH-101 (FMC) | Diluent | 30.5 | 12.2 | 36.6 |
| | Citric Acid Monohydrate Powder (Spectrum) | Acidifier | 67.5 | 27.0 | 81 |
| | Co-processed Starch STARCAP ® 1500 (Colorcon) | Diluent/binder | 30 | 12.0 | 36 |
| | Hypromellose METHOCEL ® E50 (Dow) | Matrix Polymer | 50.0 | 20.0 | 60 |
| Extragranular[2] | PROSOLV ® HD90 (JRS Pharma) | Diluent | 55.0 | 22.0 | 66 |
| | CAB-O-SIL ® M-5P (Cabot) | Glidant | 1.25 | 0.5 | 1.5[b] |
| | Magnesium Stearate (Veg. Source, Product Code 2257), NF/EP/JP | Lubricant | 1.25 | 0.5 | 1.5[b] |
| | Total | | 250.0 | 100.0% | 300 g |

[1] Removed upon drying
[2] Adjusted based on granulation yield

TABLE 3

Melatonin 2 mg Extended Release Prototype Final Blend Physical Properties

| Bulk Density | 0.43 g/mL |
|---|---|
| Tap Density | 0.50 g/mL |
| Compressibility | 14.4% |
| Flodex Flow | 16 mm critical orifice |

| Sieve Analysis | % Retained |
|---|---|
| 600 μm | 19.8 |
| 425 μm | 15.1 |
| 300 μm | 10.0 |
| 180 μm | 16.5 |
| 106 μm | 20.6 |
| 45 μm | 17.1 |
| <45 μm | 0.1 |

TABLE 4

Properties of Melatonin 2 mg Extended Release Tablet-
Prototype Lot CYV45-002-048A

| Property | Results |
|---|---|
| Tablet Press | Eight station Picolla B/D press (one station used) |
| Tablet Tooling | FDL-041: 0.455" × 0.190" capsule shaped, plain faced |
| Tablet Press Speed | 40 rpm |
| Main compression Force | 4.2 kiloNewtons |
| Precompression | Not used |
| Ejection Force | 92 Newtons |
| Mean Tablet weight* | 251 mg (range 249-253 mg % RSD = 0.5) |
| Mean Tablet Hardness* | 3.9 (range 3.4-4.2, % RSD = 6.2) |
| Mean Tablet Thickness* | 0.196" (range 0.195-0.196", % RSD = 0.2) |
| Tablet Friability | 0.03% for 100 drops |

*10 tablets chosen at random from compression of 300 g batch

TABLE 5

Melatonin Assay/Related Substances of 2 mg Melatonin
Extended Release Tablets Lot CYV45-002-048A

| | |
|---|---|
| Melatonin Assay | 105.2% |
| Reportable impurities (>0.10%) | 0.18% @RRT 1.47 |
| Total Impurities | 1.8% |

TABLE 6

Composition of Final Tablet

| Materials Vendor/Lot # | 2 mg Tablet | % w/w | g/Batch |
|---|---|---|---|
| Purified Water | NA$^a$ | NA$^a$ | 58 g for PEG solution + 157 g for granulation$^a$ |
| Melatonin | 2.0 | 0.8 | 8.0 |
| PEG8000 | 12.5 | 5.0 | 50.0 |
| Microcrystalline Cellulose, NF AVICEL ® PH102 | 144.25 | 57.7 | 577.0 |
| Citric Acid Powder | 12.5 | 5.0 | 50.0 |
| Hypromellose METHOCEL ® E50 | 75.0 | 30.0 | 300 |
| CAB-O-SIL ® Colloidal Silicon Dioxide | 1.25 | 0.5 | 5.0 |
| Magnesium Stearatre | 2.50 | 1.0 | 10.0 |
| Total Prior to Coating | 250.0 | 100.0% | 1000 g |

$^a$Water was used as a solvent and granulation fluid and was removed during processing.

Example 2

Melatonin and Valerian Composition

In this prospective example, the composition includes valerian in combination with melatonin. The composition is prepared as a two-part dosage form. The dosage form includes an expedited release portion and a sustained release portion. The contents of the valerian product are summarized in Table 7. SR indicates that the ingredient is part of the sustained release portion. ER indicates that the ingredient is part of the expedited release portion.

TABLE 7

Contents of dosage form

| Portion | Ingredient | Mass (mg) | % w/w of portion | % w/w of dosage form |
|---|---|---|---|---|
| SR intragranular | Valerian root extract | 200 | 39.1 | 21 |
| SR intragranular | melatonin | 5 | 0.1 | 5 |
| SR intragranular | Hypromellose (PHARMACOAT ® 615) | 28 | 5.5 | 3 |
| SR intragranular | Citric acid | 75 | 14.7 | 8 |
| SR extragranular | MCC | 150 | 29.4 | 16 |
| SR extragranular | Hypromellose (METHOCEL ® K4M) | 50 | 9.8 | 5.4 |
| SR extragranular | Silicon dioxide | 2.5 | 0.49 | 0.27 |
| | | 510.5 | | |
| ER extragranular | WWB extract | 263 | 62.5 | 28 |
| ER extragranular | Silicified MCC | 150 | 35.7 | 16 |
| ER extragranular | Mg stearate | 7.5 | 1.8 | 0.8 |
| | | 420.5 | | |
| | TOTAL WEIGHT | 931 | | |

The sustained release portion is prepared via a spray granulation process, such as top spray or tangential spray fluidized bed granulation process. In this process, granules containing the valerian root extract, melatonin, and PHARMACOAT® 615 hypromellose are prepared. The pH of the granules is between 3.3-5. The microcrystalline cellulose (MCC), METHOCEL® K4M hypromellose and silicon dioxide are external to the granules.

In the sustained release portion, intragranular hypromellose provides the polymer matrix and also functions as a moisture and oxygen barrier to prevent oxidative degradation of the melatonin and valerian root extract.

The expedited release portion is designed to release about 10% to about 25% of the valerian root extract and melatonin within about one after oral ingestion and the remaining melatonin and valerian over the following 5 to 7 hours after oral ingestion.

The expedited release portion is prepared by combining the 98% salicin white willow bark extract, silicified MCC and magnesium stearate. The expedited release portion is designed to release substantially all of the white willow bark extract within about 30 minutes to 1 hour after oral ingestion.

The expedited release and sustained release portions are compressed together into a bi-layer tablet or compressed individually to form two smaller tablets. The tablets are finish coated with hypromellose or polyvinylpyrrolidone for further stability protection and to help with swallowing.

Example 3

Melatonin, Valerian, and Salicin Composition

The product in this example is similar to that of Example 1, except that the expedited release portion includes granules including the valerian root extract, PHARMACOAT® 615 hypromellose, and citric acid. The contents of this valerian product are summarized in Table 8.

TABLE 8

Contents of dosage form

| Portion | Ingredient | Mass (mg) | % w/w of portion | % w/w of dosage form |
|---|---|---|---|---|
| SR intragranular | Valerian root extract | 100 | 25.9 | 10 |
| SR intragranular | melatonin | 5 | 0.1 | 5 |
| SR intragranular | Hypromellose (PHARMACOAT ® 615) | 14 | 36 | 1.4 |
| SR intragranular | Citric acid | 65 | 16.8 | 6.6 |
| SR extragranular | MCC | 150 | 29.4 | 16 |
| SR extragranular | Hypromellose (METHOCEL ® K4M) | 50 | 9.8 | 5.4 |
| SR extragranular | Silicon dioxide | 2.5 | 0.49 | 0.27 |
| | | 386.5 | | |
| ER intragranular | Valerian root extract | 100 | 17 | 10 |
| ER intragranular | Hypromellose (PHARMACOAT ® 615) | 14 | 23 | 1.4 |
| ER intragranular | Citric acid | 65 | 11 | 6.6 |
| ER extragranular | WWB extract | 263 | 62.5 | 28 |
| ER extragranular | Silicified MCC | 150 | 35.7 | 16 |
| ER extragranular | Mg stearate | 7.5 | 1.8 | 0.8 |
| | | 599.5 | | |
| | TOTAL WEIGHT | 986 | | |

Compared to the product in Example 2, this valerian product shifts half of the valerian dose to the expedited release portion.

The expedited release portion is designed to release substantially all of the white willow bark extract and valerian root extract in it within about 30 minutes to 1 hour after oral ingestion.

This disclosure has described example embodiments, but not all possible embodiments of the valerian product or associated methods. Where a particular feature is disclosed in the context of a particular embodiment, that feature can also be used, to the extent possible, in combination with and/or in the context of other embodiments. The valerian product and related methods may be embodied in many different forms and should not be construed as limited to only the embodiments described here.

That which is claimed is:

1. A composition comprising an oral pharmaceutical dosage form having:
    a solid core including a combination of melatonin and a GABA receptor agonist ingredient located together within a first acidified polymeric matrix;
    an expedited release portion including 5% to 50% of the GABA receptor agonist ingredient in the pharmaceutical dosage form, the expedited release portion being effective to release substantially all of the GABA receptor agonist ingredient therein within about 2 hours from placement in a 0.1 N HCl solution; and
    a sustained release portion including the remainder of the GABA receptor agonist ingredient in the pharmaceutical dosage form, the sustained release portion being effective to release substantially all of the GABA receptor agonist ingredient therein from at least 5 to about 8 hours from placement in a phosphate buffer with a pH of 6.8.

2. The composition of claim 1, wherein the first acidified polymeric matrix has a pH of about 1 to about 4.4.

3. The composition of claim 1, wherein the sustained release portion includes a plurality of individual granules that have the remainder of the GABA receptor agonist ingredient in the pharmaceutical dosage form therein.

4. The composition of claim 1, further comprising an analgesic ingredient in the expedited release portion.

5. The composition of claim 1, further comprising an analgesic ingredient in the expedited release portion; and
    wherein the sustained release portion includes a plurality of individual granules that have the remainder of the GABA receptor agonist ingredient in the pharmaceutical dosage form therein.

6. The composition of claim 1, wherein the GABA receptor agonist ingredient includes valerian and the expedited release portion further includes an analgesic ingredient.

7. The composition of claim 1, wherein the GABA receptor agonist ingredient includes valerian and the expedited release portion further includes an analgesic ingredient having salicin therein.

8. The composition of claim 1, wherein the pharmaceutical dosage form is at least one of a compressed tablet, capsule, and multiparticulate-containing oral dosage form.

9. The composition of claim 1, wherein, in the expedited release portion, the 5% to 50% of the GABA receptor agonist ingredient in the pharmaceutical dosage form is located within a second acidified polymeric matrix having a pH of about 1 to about 4.4.

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 1

Tyr Leu Gly Tyr Leu Glu Gln Leu Leu Arg
1               5                   10
```

10. A composition comprising a pharmaceutical dosage form having:
- a solid core including a combination of melatonin and an analgesic ingredient, the melatonin being located within a first acidified polymeric matrix with a GABA receptor agonist ingredient;
- an expedited release portion including 5% to 50% of the analgesic ingredient and the melatonin in the pharmaceutical dosage form, the expedited release portion being effective to release substantially all of the analgesic ingredient and melatonin therein within about 2 hours from placement in a 0.1 N HCl solution; and
- a sustained release portion including the remainder of the analgesic ingredient and melatonin in the pharmaceutical dosage form, the sustained release portion being effective to release substantially all of the analgesic ingredient and melatonin therein from at least 5 to about 8 hours from placement in a phosphate buffer with a pH of 6.8.

11. The composition of claim 10, wherein the first acidified polymeric matrix has a pH of about 1 to about 4.4.

12. The composition of claim 10, wherein the sustained release portion includes a plurality of individual granules that have the remainder of the melatonin in the pharmaceutical dosage form therein.

13. The composition of claim 10, wherein the analgesic ingredient includes a salicin source.

14. The composition of claim 13, wherein the salicin source is a white willow bark extract that is at least about 75% salicin.

15. The composition of claim 10, wherein the pharmaceutical dosage form is at least one of a compressed tablet, capsule, and multiparticulate-containing oral dosage form.

16. The composition of claim 10, wherein, in the expedited release portion, the 5% to 50% of the analgesic ingredient in the pharmaceutical dosage form is located within a second acidified polymeric matrix having a pH of 1 to 4.4.

* * * * *